United States Patent [19]
Strelow et al.

[11] Patent Number: 6,077,895
[45] Date of Patent: *Jun. 20, 2000

[54] PH SENSITIVE THERMOPLASTIC BINDER

[75] Inventors: Diane Strelow, Waukesha; Mark Alper, Mukwonago, both of Wis.

[73] Assignee: Ato Findley, Inc., Wauwatosa, Wis.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/763,167

[22] Filed: Dec. 10, 1996

Related U.S. Application Data

[63] Continuation of application No. 08/512,088, Aug. 7, 1995, abandoned, which is a continuation-in-part of application No. 08/091,968, Jul. 15, 1993, Pat. No. 5,527,845.

[51] Int. Cl.⁷ .............................. C08L 91/06; C08L 59/00; C08L 31/02; C08K 5/12
[52] U.S. Cl. .................... 524/272; 524/270; 524/292; 524/296; 524/141; 524/508; 524/512; 524/515; 524/522; 524/523; 428/349; 428/288; 428/326
[58] Field of Search .................... 524/270, 272, 524/292, 296, 141, 512, 515, 508, 522, 523; 428/347, 288, 326

[56] References Cited

U.S. PATENT DOCUMENTS

| | | | |
|---|---|---|---|
| 2,657,189 | 10/1953 | Pinkney | 524/471 |
| 3,337,485 | 8/1967 | Lawrence et al. | 524/272 |
| 3,644,267 | 2/1972 | Jackson, Jr. et al. | 523/514 |
| 4,100,324 | 7/1978 | Anderson et al. | 428/288 |
| 4,283,317 | 8/1981 | Murphy et al. | 524/272 |
| 4,284,541 | 8/1981 | Takeda et al. | 524/272 |
| 4,284,542 | 8/1981 | Boyce et al. | 524/270 |
| 4,289,669 | 9/1981 | Lakshmanan | 524/272 |
| 4,434,261 | 2/1984 | Brugel et al. | 524/425 |
| 4,459,129 | 7/1984 | Gooding et al. | 524/272 |
| 4,631,308 | 12/1986 | Graham et al. | 524/272 |
| 4,654,389 | 3/1987 | Graham et al. | 524/272 |
| 4,656,213 | 4/1987 | Schlademan | 524/272 |
| 5,180,620 | 1/1993 | Mende | 428/138 |
| 5,183,841 | 2/1993 | Bernard | 524/272 |
| 5,238,733 | 8/1993 | Joseph | 428/284 |
| 5,242,981 | 9/1993 | Izumi et al. | 525/133 |
| 5,318,813 | 6/1994 | Flexman, Jr. | 525/131 |
| 5,324,610 | 6/1994 | Tanaka et al. | 430/83 |
| 5,385,965 | 1/1995 | Bernard et al. | 524/272 |
| 5,387,623 | 2/1995 | Ryan et al. | 523/124 |

FOREIGN PATENT DOCUMENTS

| 0481467 | 5/1997 | European Pat. Off. . | |
| 0638610 | 12/1978 | Russian Federation | 524/272 |

*Primary Examiner*—Peter A. Szekely
*Attorney, Agent, or Firm*—Andrus, Sceales, Starke & Sawall

[57] ABSTRACT

An alkali soluble hot melt composition for melt blowing applications is described which maintains a viscosity of at least 50,000 cp at temperatures of 350° F. The adhesive composition in cludes about 20% to about 95%, by weight, of an alkali soluble polymer; about 0% to about 50%, by weight, of a crystalline resin; about 0–50% by weight, of a suitable filler; and about 0% to about 50%, by weight, of a suitable plasticizer.

7 Claims, No Drawings

PH SENSITIVE THERMOPLASTIC BINDER

This application is a continuation of application Ser. No. 08/512,088 filed Aug. 7, 1995, now abandoned. In which this application is a continuation-in-part of copending application Ser. No. 08/091,968, filed Jul. 15, 1993, now U.S. Pat. No. 5,527,845.

FIELD OF THE INVENTION

This invention relates to hot melt polymeric compositions which can be used as binders in the production of melt blown fabrics having utility as disposable soft goods such as diapers, fabric sheets or wipes.

More specifically, the invention relates to such compositions which form binders that can be readily dispersed after use so that a material such as fibers cohered or adhered by the hot melt composition can be separated, for example, for recycling.

BACKGROUND OF THE INVENTION

Hot melt compositions have heretofore frequently been used as binders or adhesives. One important use of such materials is in the production of melt blown fabrics. Examples of such fabrics and methods for producing the same are set forth, for example, in Anderson et al. U.S. Pat. No. 4,100,324, issued Jul. 11, 1978. As set forth in that disclosure, the thermoplastic polymers preferred for use as binders include polyolefins, polyamides, polyesters such as polyethylene teraphthalate and thermoplastic polyurethane elastomers. Many of these materials can be used to make melt blown fabrics having suitable tensile strength and fabric properties, for example, used as wipes for various purposes. After the fabric has been used, the wipe or other article is generally disposed of in a landfill.

Because of the desirability of having the capability of recycling the fibers which make up fabrics such as those used as wipes, thus saving the resources used in forming the fabrics and in reduction of volume of materials placed in landfills, a need has existed for improved binder compositions. Specifically, a binder that would retain strength and integrity during the course of intended use which could readily be dissolved for reuse of the components would be highly desirable.

As already noted, hot melt compositions based on polymers such as polyolefins, polyamides, polyurethanes or polyesters have been used to produce nonwoven fabrics by melt blown spray procedures. In such cases, the binder polymer is used to bind fibers which may be formed of synthetic materials or natural materials such as cellulosic fibers. Such fabrics are useful for wipes used in various ways. Currently used binders do not facilitate recycling or easy disposal of used fabrics, which thus generally end up in a landfill.

A need has, thus, existed for improved binders for melt blown fabrics which would have acceptable tensile strength yet could be disposed of by easy disintegration into the component parts.

SUMMARY OF THE INVENTION

It is an important object of the present invention to provide a hot melt composition capable of use in melt blowing procedures using available melt blowing equipment, and which is stable under neutral or acidic conditions but which breaks down under alkaline conditions. In accordance with a related object of the invention, a composition is provided suitable as a thermoplastic binder for other fibers used in composite melt blown fabrics and which forms a binder providing integrity to the resulting fabric. In accordance with a further related aspect of the invention, the hot melt composition can be melt blown and incorporated with staple fibers, for example, absorbent fibers, using conventional procedures, to form fabrics having various compositions and characteristics.

In accordance with a yet further related aspect of the invention, the staple fibers used in formation of hot melt fabrics may be natural materials or synthetic polymers such as polyolefins. In accordance with a still further aspect of the invention, the resultant fabrics can be used as wipes in various applications.

An important advantage of the present invention is that the fabrics bound together with the composition of the invention provide unique opportunities for disposal thereof by placing the wipe or other object formed from the fabric in an alkaline or mildly basic solution. In accordance with a related aspect, the hot melt composition binding the fabric together, breaks down in basic solutions thus allowing the fabric to disintegrate into its component fibers. In accordance with a still further aspect of the invention, the properties of the hot melt composition can be varied in order to provide fabrics that are dispersible at a preselected pH range, for example, above about 7, or above about 9, dependent on the end use requirements of a specific end product. After dispersion and separation there from of the hot melt blown fibers, the staple fibers can be separated, flushed or recycled.

In accordance with the invention, the composition is based on a thermoplastic polymer suitable for hot melt applications. The preferred constituents include alkali soluble polymers selected from polyacrylates, polymethacrylates and styrene copolymers of polyacrylates or polymethacrylates, which will dissolve under basic conditions, i.e., a pH of greater than about 7. The materials are stable under neutral or mildly acidic conditions but dissolve or disperse in aqueous liquids having a pH greater than about 7 and, for some applications, preferably in the range of 9 or greater.

It is, therefore, an object of the present invention to provide improved hot melt compositions which are uniquely well suited for the manufacture of disposable soft goods such as fabrics and wipes.

It is a further object of the present invention to provide a hot melt composition which can be employed as a binder in melt blown operations using available existing equipment.

In accordance with preferred embodiments of the invention, various optional ingredients are included with the base polymer. These ingredients preferably include an antioxidant in the range of 0.1–3%. A filler of up to 50% which are preferably finely divided inert inorganic materials such as calcium carbonate or finely divided silica. A crystalline resin preferably included in an amount up to about 50%. A plasticizer can also be added in amounts up to about 50% by weight of the composition.

In accordance with an important aspect of the present invention a hot melt composition with a viscosity suitable for melt blowing is based on:

(a) about 20% to about 95%, by weight, of an alkali soluble polymer;

(b) about 0% to about 50%, by weight, of a compatible crystalline resin;

(c) about 0% to about 50%, by weight, of a suitable plasticizer;

(d) about 0% to 50% of a particulate inorganic filler; and (e) about 0% to about 3%, by weight, of an antioxidant, and wherein the hot melt composition solubilizes or disperses when exposed to an aqueous solution having a pH greater than a preselected pH above about 7 for a predetermined period of time.

Another further object of the invention is to provide a hot melt binder composition which an be employed in connection with the manufacture of disposable soft goods, and wherein the hot melt composition has an excellent dry tensile strength but which can be induced to dissolve or disperse in an alkaline liquid thereby permitting the component elements of the disposable soft good to be recycled or otherwise disposed of in an environmentally friendly manner.

Another object of the present invention is to provide a binder composition wherein the alkali soluble polymer is a polyacrylate, a polymethacrylate, a styrene copolymer with polyacrylates or polymethacrylates or an acrylic acid/acrylic ester copolymer.

Another object of the present invention is to provide a hot melt composition which binds or encompasses staple fibers to form a fabric which does not substantially degrade when exposed to water acidic solutions or urine, but which readily solubilizes when exposed to a solution having a preselected pH greater than about 7 for a predetermined period of time.

A still further object of the present invention is to provide a hot melt composition which has a viscosity suitable for use in melt blowing procedures. In accordance with a preferred embodiment, the composition maintains a viscosity greater than about 50,000 centipoise at elevated temperatures of as high as 350° F.

Another object of the present invention is to provide a hot melt composition which possesses an excellent balance of high cohesive strength and viscosity at elevated temperatures and an ability to bind or capture various fibers into fabrics having integrity under acidic or neutral conditions.

Further objects and advantages of the present invention will be apparent from the following detailed description, examples and claims.

DESCRIPTION OF THE PREFERRED EMBODIMENT

The preferred hot melt composition of the present invention, as noted above includes, about 20% to about 95%, by weight, of an alkali soluble polymer; about 0% to 50%, by weight, of a compatible crystalline resin; about 0% to about 50%, by weight, of a suitable plasticizer, about 0% to 50% of a particulate inorganic filler and about 0% to 3%, by weight, of an antioxidant and wherein the hot melt adhesive composition solubilizes when exposed to a solution having a pH greater than a preselected number for a predetermined period; modifying additives such as poly (vinyl methyl ether) may be optionally included in minor amounts, if desired.

The composition of the present invention includes, about 20% to about 95%, by weight, of an alkali soluble polymer which is selected from the group which includes polyacrylates, polymethacrylates, styrene copolymers with polyacrylates or polymethacrylates, or an acrylic acid/ acrylic ester copolymer. Suitable alkali soluble polymers may be purchased commercially from Belland, Inc. of Andover, Massachusetts under the trade designation KBC 2026 SA; KBC 2180 SA and; KBC 4120 HA, KBC 2600, 2620, G30.

It will also be recognized that mixtures of the above identified polymers may also be utilized in the present formulations.

The hot melt adhesive composition of the present invention also may include, as noted above, about 0 to 30%, by weight, of a poly (vinyl methyl ether) or other compatible polymer. This component of the adhesive composition is utilized to modify the viscosity, crystallinity, tack, melt strength and other characteristics of the composition with respect to ability to use the same in melt blowing processes, as needed in connection with a particular alkali soluble polymer blend. The poly (vinyl methyl ether) can be purchased commercially from the Amoco Chemical Company of Chicago, Ill., under the trade designation "Amobond". In many applications, the poly (vinyl methyl ether) may not be necessary.

The present formulation includes about 0% to about 50% by weight of a compatible crystalline resin which is selected from the group which includes polymerized rosin; partially hydrogenated rosin; terpene phenolic resins, styrene acrylic resins; ethylene acrylic acid and partial esters of dibasic modified tall oil rosin. Commercially available polymerized rosins may be secured from Arizona Chemical Company under the trade designations "Sylvatac 295, RX, R85, 95, and 140", respectively. Additionally, Hercules Chemical Company, Inc. produces a suitable polymerized rosin under the trade designation "PolyPale Resin". Commercially suitable partially hydrogenated rosins may be secured from the Hercules, Inc. under the trade designations "Foral AX" and "Stabelite". Commercially suitable terpene phenolics may be secured form the Arizona Chemical Company under the trade designations "Nirez V2040" and "V2150", respectively. Finally, partial esters of dibasic modified tall oil rosins may be secured from Arizona Chemical Company under the trade designation "Sylvatac 203" and "Beckacite 4901". Other crystalline resins such as styrene acrylic resins, for example, Carboset GA1160 available from B. F. Goodrich, can also be employed for this purpose. Other additive resins such as ethylene acrylic acid, available from Dow Chemical Co. under the trade designation Primacore 5980I may be included to increase flex strength and elasticity.

A plasticizer may be included in the composition of the present invention in amounts up to about 50%, by weight. A suitable plasticizer may be selected from the group which includes dipropylene glycol dibenzoate; pentaerythritol tetrabenzoate; 2-ethylhexyl diphenyl phosphate; and butyl benzyl phthalate. Suitable dipropylene glycol dibenzoate and pentaerythritol tetrabenzoate may be purchased form the Velsicol Chemical Company of Chicago, Ill., under the trade designations "Bensoflex 9-88 and S-552", respectively. Finally, a suitable 2-ethylhexyl diphenyl phosphate, and a butyl benzyl phthalate may be purchased from the Monsanto Industrial Chemical Company of St. Louis, Mo., under the trade designation "Santicizer 141 and 160", respectively.

The present invention may optionally include a stabilizer/ antioxidant. The stabilizers which are useful in the hot melt compositions of the present invention are incorporated to help protect the polymers noted above, and thereby the total adhesive system, from the effects of thermal and oxidative degradation which normally occurs during the manufacture and melt blowing of the composition as well as in the ordinary exposure of the final product to the ambient environment. Such degradation is usually manifested by a deterioration in the appearance, physical properties and performance characteristics of the composition. Among the applicable stabilizers are high molecular weight hindered phenols and multi-functional phenols, such as sulfur and phosphorous containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted on the benzene ring in at least on top the ortho positions relative to the phenolic hydroxyl group. The presence of these sterically bulky substituted radicals in the vicinity of the hydroxyl group serves to retard its stretching frequency and correspondingly, its reactivity; this stearic hindrance thus providing the phenolic compound with its stabilizing properties. Representative hindered phenols include:

1,3,5-trimethyl-2,4,6-tris(3-5-ditertbutyl-4-hydroxybenzyl) benzene;

pentaerythritol tetrakis-3(3.5-di-tertbutyl-4-hydroxyphenyl) propionate;

n-octadecyl-3(3,5-di-tert-butyl-4-hydroxyphenyl) propionate;

4,4'-methylenebis(4-methyl-6-tert butylphenol);

4,4'-thiobis(6-tert-butyl-o-cresol);

2, 6-di-tert-butylphenol;

6-(4-hydroxyphenoxy_-2,4-bis(n-ocythlthio)-1,3,5-triazine;

di-n-octadecyl-3,5-di-ter-butyl-4-hydroxybenzoate; and sorbitol hexa-(3,3,5-di-tert-butyl-4-hydroxy-phenyl) propionate.

Especially preferred as a stabilizer is pentaerythritol tetrakis-3(3,5-di-tert-butyl-4-hydroxyphenyl) propionate.

The performance of these stabilizers may be further enhanced by utilizing, in conjunction there with; (1) synergists, for example, as thiodipropionate esters and phosphites; and (2) chelating agents and metal deactivators as, for example, eethylenediaminetetraacetic acid, salts thereof, and disalicylalpropylenedieimine. These stabilizers may be purchased from any one of the several chemical companies noted earlier.

Particulate inorganic fillers such as calcium carbonate, surface modified calcium carbonate, titanium dioxide, silica, or surface treated wollastonite (calcium silicate) with a particle size of less than 10 microns, preferably less than 1 micron can be added to modify the characteristics of the composition. These fillers are added to the formulation, to reduce tack, increase viscosity, increase internal strength, reduce cost, and potentially reduce odor and color of the hot melt. These fillers can be used to tailor the hot melt blend to the properties needed for the specific application.

The hot melt compositions of the present invention may be formulated using any of the techniques known in the art. A representative example of a known procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 300° F. to 450° F. It should be understood that the precise temperature to be used in this step would depend on the melting point of the particular ingredients. The resulting composition is agitated until the polymers completely dissolve. A vacuum is then applied to remove any entrapped air.

Other types of mixing equipment can also be employed, for example, a kneading type mixer or twin screw extruder, if desired.

It should be understood that other optional additives may be incorporated into the adhesive composition of the present invention in order to modify particular physical properties. These may include, for example, such materials as colorants or pigments.

The hot melt compositions of this invention are soluble or dispersible in an aqueous solution having a preselected pH greater than about 7. The pH at which the composition disperses can be modified by use of different alkali souble polymers and by varying the proportions of the additives described hereinabove. Suitable aqueous solutions for dispersion of the compositions are provided by use of $NH_4OH$, KOH, NaOH, $Na_2CO_3$, or $K_2CO_3$ in water. In some applications it may be desirable to provide a fabric which disperses at pH's in the 7 to 8 range, while in other applications it may be desirable to provide a fabric stable in neutral solutions which will disperse at a preselected pH over 9.

The invention is further illustrated by way of the following examples. Each of the adhesive examples was manufactured by the general procedure described above.

The invention will be further set forth in the following Examples wherein all parts or percentages are given by weight unless otherwise indicated.

EXAMPLE 1

The following ingredients were blended at 350° F to form a homogeneous mixture:

45% Belland G30-A61 polymer (Belland, Andover MA);

25% Carboset GA-1160 (B.F. Goodrich, Cleveland, Ohio);

18% Benzoflex 9-88 plasticizer [Velsicol, Rosemont, IL];

10% Camel-CAL [Genstar Stone Products, Hunts Valley, MD]

2% Irganox 1010 [Ciba Geigy, Hawthorne, NY]

This formulation has a viscosity of about 200,000 CP at 350° F., and, when melt blown together with cellulosic fibers using the equipment described in the above-noted Anderson et al '324 patent at 375° F. does a good job of fabric fiber capture, forming a fabric with adequate tensile strength for wipe use. This formulation is stable under acidic conditions and disperses after 10 minutes at pH 7.5.

Example 2

The following ingredients were blended as in Example 1:

25% Belland G30-A61 polymer

30% Carboset GA-1160

15% Dow Primacore 5980I

10% Camel-Cal

18% Benzoflex 9-88

2% Irganox 1010

The viscosity @ 350°°F. was 109,000 centipoise. The formulation can be melt blown as in Example 1 to provide fabrics having improved flexibility and tensile strength.

Example 3

The following ingredients were blended as in Example 1:

10% Carboset GA-1160

15% Belland KBC 2026SA

68% Belland GBE 2620 AA

5% Benzoflex S-352

2% Iraanox 1010

The viscosity @ 350°°F. was 80,000 centipoise. The formulation can be melt blown as in Example 1.

It will be apparent to those skilled in the art that the foregoing examples have been made for purposes of illustration and that variations may be made in proportions, procedures and material without departing from the scope of the present invention. Therefore, it is intended that this invention not be limited except by the claims which follow.

What is claimed is:

1. A hot melt composition suitable for formation into microfibers by melt blowing procedures comprising:

about 20% to about 95%, by weight, of an alkali soluble polymer, where the repeating unit of said alkali soluble polymer is selected from the group consisting of acrylic acid, methacrylic acid, acrylic ester, methacrylic ester, styrene and acrylic acid, styrene and methacrylic acid, styrene and acrylic ester, and styrene and methacrylic ester, said alkali soluble polymer having a viscosity greater than 500,000 cp at 350° F.;

about 10–50%, by weight of a compatible tackifying resin, said tackifying resin functioning as a solvent for said polymer and selected from the group consisting of a terpene phenolic tackifying resin, and a styrene acrylic tackifying resin, said tackifying resin having a viscosity less than 50,000 cp at 350° F.;

about 0–30%, by weight, of ethylene acrylic acid polymer or ethylene methacrylic acid polymer;

about 0–50%, by weight, of a suitable plasticizer;

about 0–50%, by weight, of a filler; and an antioxidant in the amount of about 0.1 to 3%;

and wherein the hot melt composition solubilizes when exposed to an aqueous solution having a pH greater than about 7 for a predetermined period of time, and said composition having a viscosity at 350° F. of at least 50,000 cp; and wherein the combined total weight of the resin, the plasticizer and the filler is from about 5% to about 80% of the total hot melt composition, and the combined total weight of all ingredients is 100% of the total hot melt composition.

2. A hot melt composition as claimed in claim 1 wherein the plasticizer is selected from the group consisting of dipropylene glycol dibenzoate, pentaerythritol tetrabenzoate, 2-ethylhexyl diphenyl phosphate and butyl benzyl phthalate.

3. A hot melt composition as claimed in claim 1 wherein the composition is melt blowable to form microfibers which bind a lattice of fabric together into a fabric or sheet, and wherein the hot melt composition when exposed to a solution which has a pH of 7.5 or greater solubilizes to a degree which permits separation of the component fibers.

4. A hot melt composition as claimed in claim 3 wherein the composition forms fibers having diameters less than about 10 microns.

5. A hot melt composition as claimed in claim 1 wherein the filler is selected from the group consisting of calcium carbonate, surface modified calcium carbonate, titanium dioxide, calcium silicate and surface treated calcium silicate with a particle size of less than 10 microns.

6. A hot melt composition consisting of:

about 25%, by weight, of an alkali soluble polymer wherein the repeating unit of said alkali soluble polymer is selected from the group consisting of acrylic acid, methacrylic acid, acrylic ester, methacrylic esters styrene and acrylic acid, styrene and methacrylic acid, styrene and acrylic ester, and styrene and methacrylic ester, said alkali soluble polymer having a viscosity greater than 500,000 cp at 350° F.;

about 15%, by weight, of an ethylene acrylic acid polymer;

about 30%, by weight, of a styrene acrylic tackifying resin functioning as a solvent for said polymer, said tackifying resin having a viscosity less than 50,000 cp at 350° F.;

about 10%, by weight, of a filler;

about 18%, by weight, of a plasticizer; and about 2%, by weight, of an antioxidant;

wherein said composition has a viscosity at 350° F. of about 100,000 cp; and wherein the hot melt composition solubilizes when exposed to an aqueous solution having a pH greater than about 7 for a predetermined period of time.

7. A hot melt composition suitable for formation into microfibers by melt blowing procedures comprising:

about 20% to about 95%, by weight, of an alkali soluble polymer, where the repeating unit of said alkali soluble polymer is selected from the group consisting of acrylic acid, methacrylic acid, acrylic ester, methacrylie ester, styrene and acrylic acid, styrene and methacrylic acid, styrene and acrylic ester, and styrene and methacrylic ester, said alkali soluble polymer having a viscosity greater than 500,000 cp at 350° F.;

about 10–50%, by weight, of a compatible tackifying resin, said tackifying resin functioning as a solvent for said polymer and selected from the group consisting of a terpene phenolic tackifying resin, and a styrene acrylic tackifying resin, said tackifying resin having a viscosity less than 500,000 cp at 350° F.;

about 0–30%, by weight, of ethylene acrylic acid polymer or ethylene methacrylic acid polymer;

about 0–50%, by weight, of a suitable plasticizer, said plasticizer selected from the group consisting of dipropylene glycol dibenzoate, pentaerythritol tetrabenzoate, 2-ethylhexyl diphenyl phosphate and butyl benzyl phthalate;

about 0–50%, by weight, of a filler; and about 0.1–3% of an antioxidant;

said composition having a viscosity at 350° F. of at least 50,000 cp;

and wherein the combined total weight of the resin, the plasticizer and the filler is from about 5% to about 80% of the total hot melt composition, and the combined total weight of all ingredients is 100% of the total hot melt composition;

and wherein the composition is melt blowable to form microfibers which bind a lattice of fabric together into a fabric or sheet, and wherein the hot melt composition when exposed to an aqueous solution containing $NH_4OH$, $KOH$, $NaOH$, $Na_2CO_3$, or $K_2CO_3$ which has a pH of 7.5 or greater solubilizes to a degree which permits separation of the component fibers.

* * * * *

UNITED STATES PATENT AND TRADEMARK OFFICE
CERTIFICATE OF CORRECTION

PATENT NO. : 6,077,895
DATED : June 20, 2000
INVENTOR(S) : Diane Strelow et al.

It is certified that error appears in the above-identified patent and that said Letters Patent is hereby corrected as shown below:

<u>Claim 6, column 7,</u>
Line 58, delete the word "esters" and substitute therefor --- ester, ---.

Signed and Sealed this

Eleventh Day of September, 2001

Attest:

NICHOLAS P. GODICI
Attesting Officer     Acting Director of the United States Patent and Trademark Office